United States Patent [19]

Jones et al.

[11] Patent Number: 4,992,452

[45] Date of Patent: Feb. 12, 1991

[54] CERTAIN 5-ACYL-2-(1H)-PYRIDINONES USEFUL IN TREATING CARDIAC FAILURE

[75] Inventors: Winton D. Jones; Richard C. Dage; Richard A. Schnettler, all of Cincinnati, Ohio

[73] Assignee: Merrell Dow Pharmaceuticals Inc., Cincinnati, Ohio

[21] Appl. No.: 345,751

[22] Filed: May 1, 1989

Related U.S. Application Data

[60] Continuation of Ser. No. 121,543, Nov. 17, 1987, Pat. No. 4,853,395, which is a division of Ser. No. 867,825, May 27, 1986, Pat. No. 4,731,371, which is a division of Ser. No. 594,767, Mar. 29, 1984, abandoned, and a continuation-in-part of Ser. No. 490,081, Apr. 29, 1983, Pat. No. 4,568,751.

[51] Int. Cl.⁵ ............... C07D 213/57; C07D 213/62; C07D 401/12; A61K 31/44

[52] U.S. Cl. .................... 514/335; 546/261; 546/278; 546/281; 546/283; 546/284; 546/288

[58] Field of Search ............ 546/288, 278, 281, 283, 546/284, 261; 514/335

[56] References Cited

U.S. PATENT DOCUMENTS 4,412,077 10/1983 Lesher et al. ............... 546/298
4,568,751 2/1986 Jones et al. ................. 514/336
4,731,371 3/1988 Jones et al. ................. 514/336

*Primary Examiner*—Alan L. Rotman
*Attorney, Agent, or Firm*—Michael J. Sayles

[57] ABSTRACT

Novel 5-acyl-2-(1H)-pyridinones and their use as cardiotonic agents. Typical of the compounds is 5-acetyl-1,2-dihydro-6-methyl-2-oxo-3-pyridinecarbonitrile which is prepared by condensing anionic cyano acetamide with 3-[(dimethylamino)methylenyl]-2,4-pentanedione in an inert organic solvent.

12 Claims, No Drawings

CERTAIN 5-ACYL-2-(1H)-PYRIDINONES USEFUL IN TREATING CARDIAC FAILURE

This is a continuation of application Ser. No. 121,543, filed Nov. 17, 1987; Pat. No. 4,853,385 which is a divisional of application Ser. No. 867,825, filed May 27, 1986 now U.S. Pat. No. 4,731,371; which is a divisional of U.S. Ser. No. 594,767, filed Mar. 29, 1984, now abandoned; which is a continuation-in-part of U.S. Ser. No. 490,081, filed Apr. 29, 1983, now U.S. Pat. No. 4,568,751.

This invention relates to 5-acyl-2-(1H)-pyridinones and to their use as cardiotonic agents.

More specifically, this invention relates to pharmaceutically active 5-acyl-2-(1H)-pyridinones of the formula

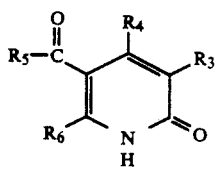

and the pharmaceutically acceptable salts thereof, wherein $R_3$ is H, —C≡N, $NH_2$, $CONH_2$ and COOR with R being hydrogen or lower alkyl, $R_4$ is hydrogen or lower alkyl, $R_5$ is phenyl, X-substituted phenyl, pyridyl, thienyl, furyl, pyrrolyl and OR wherein R is hydroxy or lower alkoxy, and X is lower alkyl, lower alkoxy, lower alkyl thio, halogen, nitro, lower alkanoyl, alkoxy carbonyl, carboxy, cyano, $NH_2$, $CONH_2$, amidino, imidazol-2-yl, and $CF_3$, and $R_6$ is hydrogen, methyl, ethyl or $R_5$. These compounds are useful as cardiotonics in the treatment of cardiac failure and other conditions requiring strengthening of heart action with a cardiotonic agent.

As used herein, the term "alkyl" includes straight, branched-chain or cyclized hydrocarbyl radicals. The term "X-substituted phenyl" include those substituents, preferably located in the para position but includes the ortho and meta substituted compounds. The term "lower" when used to modify alkyl, alkoxy, alkylthio embrace those radicals having one to six carbon atoms. Inclusive of other "x" radicals are alkoxycarbonyl (—COO lower, alkyl), lower alkanoyl (-CO-lower alkyl), amidino

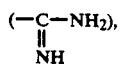

imidazol-2-yl

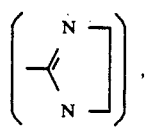

and halogeno preferably includes chloro and bromo but is embrasive of all members. The term "pyridyl" includes 2-, 3-, and 4-pyridyl, "furanyl" include 2- and 3-furanyl, "thienyl" includes 2- and 3-thienyl, and "pyrryl" includes 2- and 3-(1H)-pyrryl.

The compounds of formula I are useful both in the free base form and in the form of acid addition salts with both forms being within the purview of this invention. The acid addition salts are simply a more convenient form for use and, in practice, use of the salt amounts to use of the free base. The acids which can be used include those which produce, when combined with the free base, pharmaceutically acceptable salts, that is salts whose anions are relatively inocuous to the animal organism in pharmaceutical doses of the salts. In practice, it is convenient to form sulfate, phosphate, methansulfate or laetate salts. Others are those derived from mineral acids (e.g., hydrochloric), and organic acids such as acetic acid, citric acid, tartaric acid, ethanesulfonic acid, benzenesulfonic acid, p-toluenesulfonic acid and the like. The acid salts are prepared by standard techniques such as by dissolving the free base in aqueous or aqueous-alcohol solution or other suitable solvents containing the appropriate acid and isolating by evaporating the solution, or by reacting the free base and in an organic solvent in which case the salt separates directly or can be obtained by concentration of the solution.

In general, the compounds of this invention are prepared by standard techniques analogously known in the art. A preferred synthesis for preparing the compounds of this invention conveniently involves the reaction of an appropriate 1-$R_5$-3-$R_6$-2-(1-dimethylamino-1-$R_4$-methylidenyl)-1,3-propanedione (II) with an appropriately $R_3$ substituted acetoacetamide aCcording to standard Michael addition reaction conditions. Preferably, the substituted acetamide is reacted with sodium hydride, under argon in an inert organic solvent, (e.g., tetrahydrofuran) to form an anion which is then condensed with the diketone (II) by heating the reactants together in an inert organic solvent, preferably tetrahydrofuran and the like. Preferably, the temperature of the reaction is about 50° C. although the reaction proceeds well at temperatures between room temperature and 100° C. Heating is effected over a period of several hours although it is preferred to allow the reaction to proceed overnight. When $R_5$ and $R_6$ are not the same a mixture of products are obtained which are separated quite nicely by flash chromatography wherein the reaction product mixture is admixed with 60-200 mesh silica gel and the column is eluted with an appropriate solvent system (e.g., 35% ethylacetate—65% methylene chloride). The fractions of eluate are monitored by thin layer chromatography.

The foregoing reaction is depicted as follows:

Reaction Scheme A

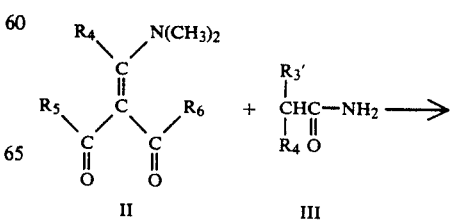

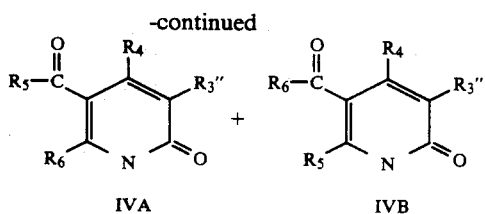

wherein R$_4$, R$_5$ and R$_6$ are as previously defined, R$_3''$ is cyano, —CO$_2$H, lower alkyl or NH$_2$; R$_3'$ is cyano, —CO$_2$H, lower alkyl or —N═CH phenyl.

The 1-R$_5$-3R$_6$-2-[(1-dimethylamino)alkylidenyl]-1,3-propanediones are readily preparated by condensing the appropriate R$_5$, R$_6$-1,3-propandiones with the appropriately R$_4$ substituted N,N-dialkylamino-dialkoxy methane (e.g., dimethylformamide acetals according to standard condensation reaction conditions such as, for example, contacting equimolar quantities of the reactants together, optionally in an inert organic solvent and stirring the mixture for 1–12 hours at about room temperature. This reaction is depicted as follows:

Reaction Scheme B

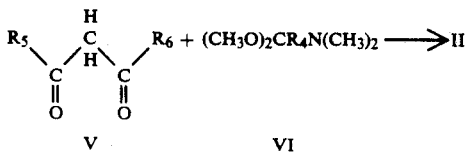

wherein R$_4$, R$_5$ and R$_6$ are as previously defined.

In those instances, wherein X is other than lower alkyl, hydroxy, alkoxy, halogen, nitro, cyano, amino, and R$_3$ is other than cyano, it is preferred to prepare a compound of formula I wherein X is cyano, and then, by the use of standard techniques, convert the cyano moiety to the desired substituents. For example, the cyano moiety may be converted to a carboxyl moiety by hydrolyzing the nitrile with 6N hydrochloric acid, sulfuric and/or other mineral acids under standard conditions such as by heating at reflux temperatures for about 12–24 hours. The carboxyl moiety may be converted to an alkoxycarbonyl moiety by the standard Fisher esterification procedure such as by heating the carboxy-containing compounds with an appropriate alcohol in the presence of an acid, e.g., 3% hydrochloric acid. The carboxamido-containing compounds may be prepared by converting the alkoxycarbonyl moiety by heating the esters in the presence of ammonia or an appropriate amine, preferably in a pressure bomb at about 100°–150° C. in an inert solvent, e.g., benzene, toluene and the like. Alternatively, the carboxamido moiety may be prepared by hydrolyzing a nitrile with concentrated sulfuric acid by heating on a steam bath at temperatures of about 50°–100° C. In those instances wherein R$_3$ is cyano, it is preferred to have the ultimately desired X substituent on the phenyl ring prior to the Michael addition reaction between the 1-R$_5$-3-R$_6$-2-(1-dimethyl-amino-1-R$_4$-methylidenyl)-1,3-propanedione and the cyano substituted acetamide.

In those instances wherein X is imidazol-2-yl, such compounds are prepared by a condensation reaction wherein the nitrile is heated to from about 150°–200° C. with ethylene diamine for about 2 hours. The amidino compounds are prepared from corresponding nitriles wherein the nitrile is converted to an imino ether which is converted to the amidino moiety by treating the imino ether with ammonia in alcohol at temperatures of about 0° C. room temperature.

In those instances wherein the R$_3$ substituent is hydrogen, it is preferred to chemically remove a cyano moiety from a compound of formula I by standard techniques such as by conversion of the cyano moiety to a carboxyl radical by treatment with a strong acid and then the compound is decarboxylated.

The preparation of the compounds of formula I may be illustrated by the following specific examples.

PREPARATION OF INTERMEDIATE
1-R$_5$-3R$_6$-2-(1DIALKYLAMINO-1-R$_4$ METHYLIDINYL)-1,3-PROPANDIONES

Example 1

2-Dimethylaminomethylenyl-1-phenyl-1,3-butandione

A mixture of 1-benzoylacetone (24.00 g, 0.15 mole) and dimethylformamide dimethylacetal were stirred overnight at room temperature under argon. The resulting reddish-colored mixture was concentrated on the rotary evaporator, then dissolved in THF (tetrahydrofuran). The resulting solution was stirred and heated to boiling and slowly diluted with hexane. At the point of turbidity heating was discontinued. An orange gum precipitated and rapidly solidified. The mixture was chilled in an ice bath and filtered yielding 25.25 g (78%) of 2-(dimethyl-amino)-1-phenyl-1,3-butanedione m.pt. 72°–74° C.

In a similar manner, by substituting the 1,3-propanediones of the foregoing example with the appropriately substituted analogs thereof and by substantially following the procedures there is produced the following intermediates:

1-(4-pyridyl)-2-(dimethylaminomethylenyl)-1,3-butandione,
1-(2-thienyl)-2-(dimethylaminomethylenyl)-1,3-butandione,
1-[2-(1-H-pyrryl)]-2-(dimethylaminomethylenyl)-1,3-butandione,
1-(3-furanyl)-2-(dimethylaminomethylenyl)-1,3-butandione,
1-(4-methoxyphenyl)-2-(dimethylaminomethylenyl)-1,3-butandione,
1-(4-methylphenyl)-2-(dimethylaminomethylenyl)-1,3-butandione,
1-(4-nitrophenyl)-2-(dimethylaminomethylenyl)-1,3-butandione,
1-(4-aminophenyl)-2-(dimethylaminomethylenyl)-1,3-butandione,
1-(2,4-dichlorophenyl)-2-(dimethylaminomethylenyl)-1,3-butandione,
1-(4-cyanophenyl)-2-[1-(dimethylamino)ethylidenyl]-1,3-butandione.

PREPARATION OF FINAL PRODUCTS

Example 2

5-Acetyl-1,2-dihydro-2-oxo-6-phenyl-3-pyridinecarbonitrile

Cyanoacetamide (2.50 g, 0.03 mole) was added to a stirred suspension of sodium hydride in (150 ml) THF and warmed to 50° C. The mixture was allowed to cool to room temperature then 3-[(dimethylamino)methylenyl]-1-phenyl-1,3-butanedione (6.52 g, 0.03 mole) dissolved in THF (20 ml) was added all at once. The suspension was heated and stirred at 50° C. overnight.

The reaction mixture was allowed to cool to room temperature, treated with acetic acid to pH 6 and concentrated on the rotary evaporator. Workup as in Example 5 gave 3.0 g of a yellow powder. The powder was mixed with 10 g of silica gel (60-200 mesh) and flash chromatographed eluting with 25% EtOAC -75% CH$_2$Cl$_2$ collecting 50 ml fractions to yield 1.1 g of 5-acetyl-1,2-dihydro-2-oxo-6-phenyl-3-pyridinecarbonitrile m.pt. 259°-261° C. in fractions 11 to 20.

Example 3

5-Benzoyl-1,2-Dihydro-6-Methyl-2-Oxo-3-pyridinecarbonitrile

The chromatography in Example 6 gave 1.1 g of 5-benzoyl-1,2-dihydro-6-methyl-2-oxo-3-pyridinecarbonitrile in fractions 24 to 40 m.pt. 265°-261° C.

Example 4

3-Cyano-1,2-Dihydro-6-Methyl-2-Oxo-5-Pyridinecarboxylic acid ethyl ester

Ethylacetoacetate (6.5 g, 0.050 mole) and dimethylformamide dimethyl acetal (7.14g, 0.060 mole) were stirred together under argon overnight. The resulting reddish oil was concentrated on the rotary evaporator and the concentrate then dissolved in THF (10 ml) and quickly added to a suspension of cyanoacetamide (4.20 g, 0.050 mole) and sodium hydride in THF (175 ml). The reaction mixture was heated and stirred overnight at 50° C. The reaction mixture was neutralized to pH 6 with acetic acid and concentrated on the rotary evaporator. The residue was triturated with a 50:50 CH$_2$Cl$_2$-H$_2$O mixture collected and recrystallized (EtOAC) giving 4.7 g of 3-cyano-1,2-dihydro-6-methyl-2-oxo-5-pyridinecarboxylic acid ethyl ester m.pt. 208°-210° C.

Example 5

6-Ethyl-1,2-Dihydro-5-[(4-Methylthio)benzoyl]-2-Oxo-3-Pyridinecarbonitrile and 5-(1-Oxopropyl)-1,2-Dihydro-6-(4-Methylthiophenyl)-2-Oxo-3-Pyridinecarbonitrile 1-[4-((methylthio)phenyl)]-1,3-pentanedione (2.66 g, 0.12 mole) and dimethylformamide dimethylacetal (1.79 g, 0.015 mole) were stirred overnight at room temperature. The resulting red oil was concentrated on the rotary evaporator and the concentrate was dissolved in THF and added to a suspension of cyanoacetamide (0.84 g, 0.010 mole) and sodium hydride (0.25 g, 0.010 mole) in THF (50 ml), and, with constant stirring heated at 50° C. for 15 hours and cooled. The mixture was brought to pH 6 with acetic acid and concentrated. The residue was dissolved in CH$_2$Cl$_2$, extracted with 5% NaHCO$_3$, washed with brine, separated, dried (MgSO$_4$) and filtered. Concentration on the rotary evaporator gave a yellow gum which upon trituration with Et$_2$O solidified. Recrystallization (EtOAC) gave 1.37 g m.pt. 208°-210° C. The HPLC (u Bondpack CN column, 55% MEOH/45% H$_2$O) showed two peaks in roughly a 40:60 ratio).

In a similar manner by utilizing the named intermediates of Example 1 and by substantially following the teachings of Examples 2-5, there are produced the following compounds.

5-(4-pyridoyl)-6-ethyl-2-oxo-1,2-dihydro-3-pyridine-carbonitrile;
5-(2-thienoyl)-6-ethyl-2-oxo-1,2-dihydro-3-pyridine-carbonitrile;
5-[2-(1H-pyrryoyl)]-6-ethyl-2-oxo-1,2-dihydro-3-pyridine-carbontrile;
5-(3-furanoyl)-6-ethyl-2-oxo-1,2-dihydro-3-pyridine-carbonitrile;
5-(2-pyridoyl)-6-ethyl-2-oxo-1,2-dihydro-3-pyridine-carbonitrile;
5-(4-methoxybenzoyl)-6-ethyl-2-oxo-1,2-dihydro-3-pyridinecarbonitrile;
5-(4-methylbenzoyl)-6-ethyl-2-oxo-1,2-dihydro-3-pyridinecarbonitrile;
5-(4-nitrobenzoyl)-6-ethyl-2-oxo-1,2-dihydro-3-pyridinecarbonitrile;
5-(4-aminobenzoyl)-6-ethyl-2-oxo-1,2-dihydro-3-pyridinecarbonitrile;
5-(2,4-dichlorobenzoyl)-6-ethyl-2-oxo-1,2-dihydro-3-pyridinecarbonitrile;
5-(4-methylthiobenzoyl)-6-ethyl-2-oxo-1,2-dihydro-3-pyridinecarbonitrile;

and the 6-methyl homologs thereof.

The compounds of general Formula 1 may be used in the treatment of cardiac failure including congestive heart failure, backward heart failure, forward heart failure, left ventricular heart failure, or right ventricular heart failure or in the treatment of any other condition which requires the strengthening of heart action with a cardiotonic.

The utility of Formula 1 compounds as cardiotonics may be determined by administering the test compound (0.01-10 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. Heart failure is induced by administering sodium pentobarbital (20 to 40 mg/kg) followed by a continuous infusion of 1-2 mg/kg/min. or propranolol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the patient, the severity of the cardiac failure and the mode of administration.

For oral or parenteral administration the cardiotonically effective amount of compound is from about 0.01 mg/kg of patients body weight per day up to about 500 mg/kg of patient body weight per day and preferably from about 0.10 mg/kg of patient body weight per day up to about 200 mg/kg of patient body weight per day.

For oral administration a unit dosage may contain, for example, from 1.0 to 750 mg of the active ingredient, preferably about 10 to 250 mg of the active ingredient. For parenteral administration a unit dosage may contain, for example, from 5 to 500 mg of the active ingredient, preferably about 10 to 250. Repetitive daily administration of the compounds may be desired and will vary with the condition of the patient and the mode of administration.

As used herein the term patient is taken to mean warm blooded animals, particularly mammals, such as humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general Formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

As is true in many large classes of compounds certain subgeneric members and certain specific members of the class are preferred for the pharmaceutical activity in treating disease states in man. In this instance the preferred compounds of formula I are those wherein $R_5$ is either phenyl or X-substituted phenyl and $R_6$ is methyl or ethyl. The preferred $R_3$ substituent is cyano or amino. The preferred $R_4$ substituent is hydrogen.

We claim:
1. A compound of the formula:

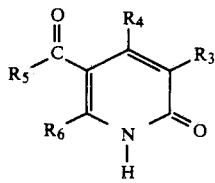

or a pharmaceutically acceptable salt thereof wherein
$R_3$ is H or —CN,
$R_4$ is hydrogen or lower alkyl,
$R_5$ is pyridyl, and
$R_6$ is hydrogen, methyl, or ethyl.

2. A method of treating cardiac failure in a patient in need thereof which comprises administering to said patient a cardiotonically effective amount of a compound of the formula:

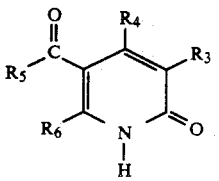

or a pharmaceutically acceptable slat thereof wherein
$R_3$ is H or —CN,
$R_4$ is hydrogen or lower alkyl,
$R_5$ is pyridyl, and
$R_6$ is hydrogen, methyl, or ethyl.

3. A compound according to claim 1 wherein $R_3$ is —CN.

4. A compound according to claim 1 which is 5-(4-pyridoyl)-6-ethyl-2-oxo-1,2-dihydro-3-pyridine-carbonitrile.

5. A compound according to claim 1 which is 5-(2-pyridoyl)-6-ethyl-2-oxo-1,2-dihydro-3-pyridine-carbonitrile.

6. A compound according to claim 1 which is 5-(4-pyridoyl)-6-ethyl-2-oxo-1,2-dihydro-3-pyridine-carbonitrile.

7. A compound according to claim 1 which is 5-(2-pyridoyl)-6-ethyl-2-oxo-1,2-dihydro-3-pyridine-carbonitrile.

8. A method of claim 2 wherein $R_3$ is —CN.

9. A method of claim 8 which is 5-(4-pyridoyl)-6-ethyl-2-oxo-1,2-dihydro-3-pyridine-carbonitrile.

10. A method of claim 8 which is 5-(2-pyridoyl)-6-ethyl-2-oxo-1,2-dihydro-3-pyridine-carbonitrile.

11. A method of claim 8 which is 5-(4-pyridoyl)-6-methyl-2-oxo-1,2-dihydro-3-pyridine-carbonitrile.

12. A method of claim 8 which is 5-(2-pyridoyl)-6-methyl-2-oxo-1,2-dihydro-3-pyridine-carbonitrile.

* * * * *